United States Patent [19]

Ademovic et al.

[11] Patent Number: 5,074,841
[45] Date of Patent: Dec. 24, 1991

[54] ATHERECTOMY DEVICE WITH HELICAL CUTTER

[75] Inventors: Martin K. Ademovic, Soquel; Ben Hidalgo, Hillsborough; John Crew, San Francisco; Simon H. Stertzer, Woodside, all of Calif.

[73] Assignee: Microcision, Inc., San Jose, Calif.

[21] Appl. No.: 472,078

[22] Filed: Jan. 30, 1990

[51] Int. Cl.⁵ .............................................. A61B 17/32
[52] U.S. Cl. ..................................... 604/22; 606/159; 606/170
[58] Field of Search ............... 606/159, 170, 171, 180; 604/22; 128/751, 752

[56] References Cited

U.S. PATENT DOCUMENTS

| | | | |
|---|---|---|---|
| 3,614,953 | 10/1971 | Moss | 606/170 |
| 4,631,052 | 12/1986 | Kensey | 606/159 |
| 4,669,469 | 6/1987 | Gifford et al. | 606/159 |
| 4,867,157 | 9/1989 | McGurk-Burleson et al. | 606/170 |
| 4,921,484 | 5/1990 | Hillstead | 606/159 |

Primary Examiner—Michael H. Thaler
Attorney, Agent, or Firm—Thomas E. Schatzel

[57] ABSTRACT

A cylindrical housing has a plurality of seriate slots. A helical cutter is rotatably mounted within the housing. A drive wire passes through the housing and connects with the cutter to provide rotational movement to the cutter. Plaque is caught between the slots and the blades of the rotating cutter, cut away from the arterial wall, ground up and flushed out through a catheter.

11 Claims, 1 Drawing Sheet

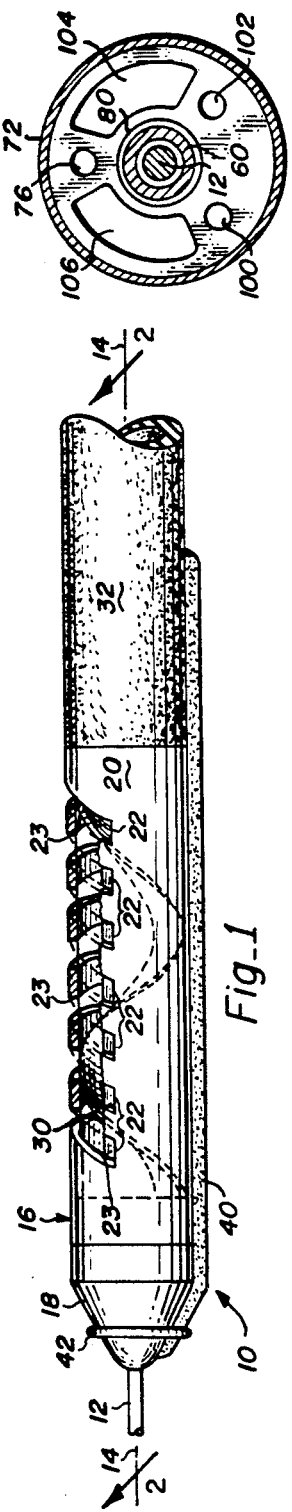
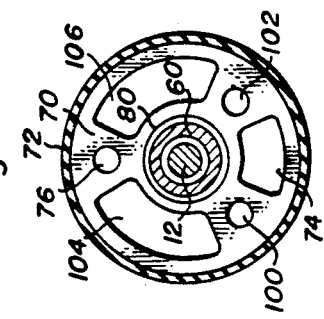
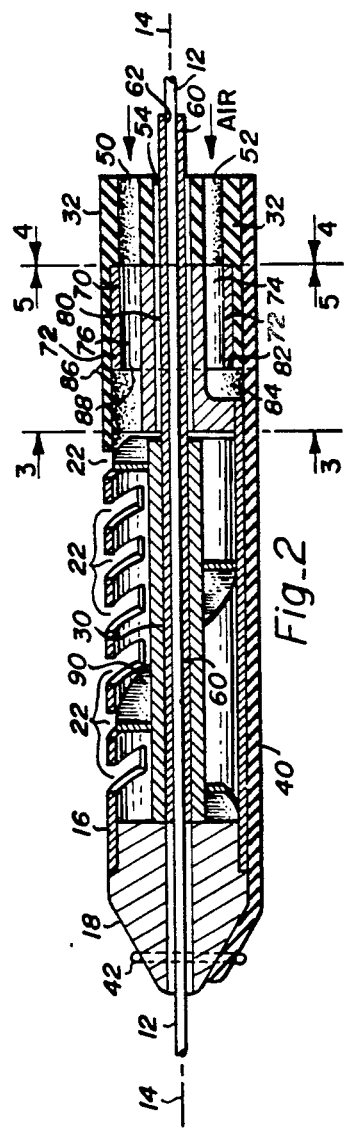
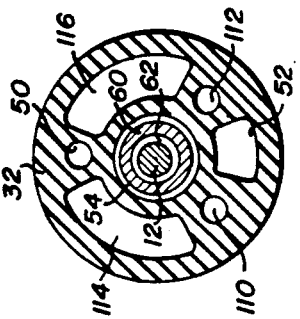
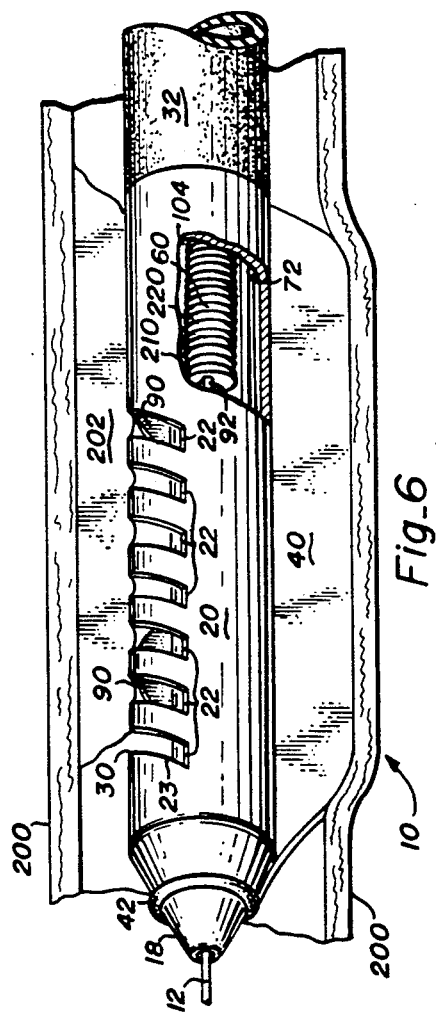

ATHERECTOMY DEVICE WITH HELICAL CUTTER

BACKGROUND OF THE INVENTION

1. Field of the Invention

This invention relates generally to atherectomy devices and more specifically to such devices with a housing having a rotating helical cutter.

2. Description of the Prior Art

One of the causes of heart disease is atherosclerosis. Atherosclerosis results when plaque builds up on the lining of the arteries. The term "plaque" refers to a number of different substances ranging from soft fat-like tissues to hard bone-like calcium deposits. Eventually, the plaque can completely block or occlude the artery and cause heart failure.

One way to treat atherosclerosis is a procedure known as an atherectomy. During an atherectomy, an incision is made in an artery and a catheter is threaded up through the artery to the position of the blockage. A tool for cutting or removing the blockage is located at the end of the catheter.

Some examples of various prior art atherectomy devices include the following: U.S. Pat. No. 4,732,154, issued to Shiber, on Mar. 22, 1988; U.S. Pat. No. 4,589,412, issued to Kensey, on May 20, 1986; U.S. Pat. No. 4,631,052, issued to Kensey, on Dec. 23, 1986; U.S. Pat. No. 4,669,469, issued to Gifford, III, et al., on Jun. 2, 1987; U.S. Pat. No. 4,690,140, issued to Mecca, on Sept. 1, 1987; U.S. Pat. No. 4,808,153, issued to Parisi, on Feb. 28, 1989; U.S. Pat. No. 4,020,847, issued to Clark, III, on May 3, 1977; U.S. Pat. No. 4,445,509, issued to Auth, on May 1, 1984; U.S. Pat. No. 4,771,774, issued to Simpson, et al, on Sept. 20, 1988; U.S. Pat. No. 4,749,376, issued to Kensey, et al, on Jun. 7, 1988; U.S. Pat. No. 4,765,332, issued to Fischell, et al, on Aug. 23, 1988; U.S. Pat. No. 4,784,636, issued to Rydell, on Nov. 15, 1988; U.S. Pat. No. 4,790,812, issued to Hawkins, Jr., et al, on Dec. 13, 1988; U.S. Pat. No. 4,790,813, issued to Kensey, on Dec. 13, 1988; U.S. Pat. No. 4,686,982, issued to Nash on Aug. 18, 1987; U.S. Pat. No. 4,729,763, issued to Henrie, on Mar. 8, 1988; U.S. Pat. No. 4,745,919, issued to Bundy, et al, on May 24, 1988; U.S. Pat. No. 4,728,319, issued to Masch, on Mar. 1, 1988; U.S. Pat. No. 4,696,667, issued to Masch, on Sept. 29, 1987; U.S. Pat. No. 4,621,636, issued to Fogarty, on Nov. 11, 1986; U.S. Pat. No. 4,273,128, and issued to Lary, on Jun. 16, 1981. The prior art also includes European patent application Publication No. 0163502A2, by Simpson and published on Apr. 12, 1985.

One problem with devices of the prior art is that they are long in length. This prevents their use in areas close to the heart because of the sharp turns in the arteries in that area. Another problem with the prior art devices is that they have trouble cutting away a flap-like piece of plaque. The flap of plaque moves as the cutting device advances and prevents the cutting device from getting a purchase or hold on the flap in order to cut it away. Another problem with the prior art devices is that they must be removed and repositioned several times during an operation in order to clean out the plaque collected. These devices typically have a small chamber to collect the plaque and this chamber must be emptied before it is full.

SUMMARY OF THE PRESENT INVENTION

It is therefore an object of the present invention to provide a compact atherectomy device with superior cutting ability.

Briefly, in a preferred embodiment, the present invention comprises a cylindrical housing having a plurality of seriate slots. A helical cutter is rotatably mounted within the housing. A drive wire passes through the housing and connects with the cutter to provide rotational movement to the cutter. Plaque is caught between the slots and the blades of the cutter and ground away from the artery wall. The ground up plaque is then pushed into flushing lumens of an attached catheter.

An advantage of the present invention is that it provides a compact atherectomy device with superior cutting ability.

These and other objects and advantages of the present invention will no doubt become obvious to those of ordinary skill in the art after having read the following detailed description of the preferred embodiment which is illustrated in the various drawing figures.

IN THE DRAWINGS

FIG. 1 is a side view of an atherectomy device of the present invention;

FIG. 2 is a cross-sectional view of the device of FIG. 1;

FIG. 3 is an end view of a portion of the device of FIG. 1;

FIG. 4 is an end view of a portion of the device of FIG. 1;

FIG. 5 is an end view of a portion of the device of FIG. 1; and

FIG. 6 is a perspective view of the device of the present invention.

DETAILED DESCRIPTION OF THE PREFERRED EMBODIMENT

FIG. 1 shows a side view of the atherectomy device of the present invention and is designated by the general reference number 10. Device 10 comprises a flexible guide wire 12 located along an axis 14. A housing 16 comprises a cap section 18 and a cylinder section 20. Sections 18 and 20 are made of stainless steel. A plurality of seriate slots 22 are located along a top side of section 20. The slots 22 have longitudinal sides 23 which are oriented at an angle of approximately 45° from axis 14. Section 20 contains a cylindrical helical cutter 30. A catheter 32 is attached to section 20 at the end opposite to cap section 18. An inflatable balloon 40 is attached to catheter 32 and section 20 by adhesive. The forward or distal portion of balloon 40 is secured to cap 18 by winding a nylon wire 42 or metal band around a recessed portion of cap section 18. Housing 16 and catheter 32 are positioned over guide wire 12.

FIG. 2 is a cross-sectional view of device 10. Catheter 32 is made of a flexible material such as low density polyethylene (LDPE). Catheter 32 has a plurality of lumens (passageways) within its diameter. A saline lumen 50 is shown about a top side of the catheter 32. A balloon lumen 52 is shown about a bottom side of catheter 32. Catheter 32 also has a central passageway 54 oriented along axis 14.

Central passageway 54 is sized to receive a cutter drive wire 60. Drive wire 60 is a flexible coiled spring wire having a central passageway 62. Passageway 62 receives guide wire 12.

Catheter 32 has a recessed portion 70 which is located at the end of catheter 32 which abuts section 20. A stainless steel cylindrical ferrule 72 fits within recessed portion 70. Ferrule 72 contains a plurality of lumens which are positioned to correspond to the lumens of catheter 32. For example, ferrule 72 has a balloon lumen 74 which aligns with balloon lumen 52 of catheter 32 and ferrule 72 has a saline lumen 76 which aligns directly with saline lumen 50 of catheter 32.

Ferrule 72 also has a central passageway 80 which is aligned along axis 14 and corresponds with central passageway 54 of catheter 32. Passageway 80 receives drive wire 60 and guide wire 12. Ferrule 72 is sized to fit within an end portion of cylinder section 20. Ferrule 72 has an aperture 82 and section 20 has an aperture 84 which align with one another to allow balloon 40 to be hermetically sealed to balloon lumen 74. Ferrule 72 has a cutter face 88. A shrink wrap 86 is applied around the junction of section 20 and catheter 32.

Helical cutter 30 is positioned within section 20. Cutter 30 has a helical blade 90. Cutter 30 has a central passageway 92 which aligns with passageway 80 of ferrule 72 and receives drive wire 60 and guide wire 12. Drive wire 60 passes through cutter 30 and is joined to cutter 30 at each end by a braze.

FIG. 3 shows an end view of ferrule 72, along the lines 3—3 of FIG. 2, on the side which has cutter face 88 and which faces section 20. In addition to saline lumen 76, there are two other saline lumens 100 and 102. Also, a pair of flushing lumens 104 and 106 pass through ferrule 72.

FIG. 4 is an end view of ferrule 72, along the line 4—4 of FIG. 2, on the side which faces catheter 32. Note that the balloon lumen 74 does not pass all the way through ferrule 72, but instead exits at the aperture 82 to the aperture 84.

FIG. 5 is a cross-sectional end view of catheter 32 taken along the line 5—5 of FIG. 2, on the side which faces ferrule 72. In addition to saline line 50, there are a couple of other saline lines 110 and 112 which correspond to saline lumens 102 and 100, respectively, of ferrule 72. A couple of flushing lumens 114 and 116 correspond to lumens 106 and 104, respectively.

FIG. 6 shows a perspective view of device 10 in operation within an artery 200. Device 10 is shown with balloon 40 inflated and with slots 22 pressing against a plaque deposit 202. The plaque deposit 202 is pushed into slots 22 and the blade 90 of rotating cutter 30 cuts off pieces of the plaque as the blade 90 pass by slots 22. The plaque pieces are forced toward the catheter end of device 10 by the rotary motion.

A cut-away portion 210 shows the end portion of ferrule 72. As the pieces of plaque are forced backward around cutter 30, they are further broken down. Finally, upon reaching ferrule 72, the plaque is squeezed between blade 90 and the face of ferrule 72 which acts as a cutting surface. The plaque is then further ground up and is forced into one of either flushing lumens 104 or 106. A stream of saline solution under pressure is delivered through saline lumens 76, 100 and 102 and enters the section 20 to help flush out the plaque. The flushing lumens 104 and 106 are aspirated to remove the plaque pieces and the saline solution.

A second cut-away 220 of cutter 30 shows the drive wire 60. The wire 60 is rotated by a motor device to turn cutter 30. One such motor device is shown in U.S. Pat. No. 4,669,469, by Gifford, III, issued Jun. 2, 1987.

The following procedure is used during an atherectomy using the present invention. First, an incision is made to the desired artery. An introducing catheter is placed through the incision. A guide catheter is then inserted through the introducing catheter. A guide wire is inserted through the guide catheter and pushed through the artery to the point of plaque blockage. The device 10 is then fed along guide wire 12 and positioned such that slots 22 face the plaque blockage. Saline solution is injected through the balloon lumen 52 of catheter 32 to inflate the balloon 40. This pushes device 10 firmly against the plaque blockage. A motor unit is then activated which rotates drive wire 60 and in turn cutter 30. Saline solution is injected through saline lumen 76, 100 and 102 as flushing lumens 104 and 106 are aspirated. The result is that the plaque deposit is cut away, ground up and flushed out through catheter 32.

The advantages of the present invention may now be understood. The prior art atherectomy devices have a small chamber to capture the plaque which has been cut-away. This chamber must be emptied before it becomes full. In a typical operation, the chamber can reach its limit after only one or two cuts. In order to empty the chamber, the entire atherectomy device must be removed from the body. This results in an increased operation time and discomfort to the patient. During an atherectomy, a flouroscope is used to view the artery. The flouroscope detects radioactive substances which are injected through the the atherectomy device saline passages. A longer operation means that more of the radioactive material must be injected into the patient.

The present invention results in a shorter operation time because it is not necessary to remove the device to clean out the plaque. The present invention uses a unique helical cutter which grinds up the plaque and allows it to be flushed out of flushing lumens in the catheter. There is no need to remove the device and clean out the plaque during the operation.

Additionally, because there is no need for a plaque holding chamber, the present device can be much shorter in length. This allows the device to be positioned in a much larger variety of arteries, including those that are closer to the heart. A further advantage of the present invention is that its helical cutter can remove flap type pieces of plaque from the artery walls.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. An atherectomy device comprising:
   a housing having at least one cutter opening, the housing comprising a shell with a longitudinal axis and a ferrule having a first end sized to fit within the interior of the shell and establishing a first surface substantially perpendicular to said longitudinal axis;
   a helical cutter positioned longitudinally within the housing with a first end of the cutter interfacing with said first surface of said ferrule and positioned to squeeze plaque between the cutter and said first surface of said ferrule so as to cut said plaque; and rotational drive means connected to the helical cutter for rotating the helical cutter.

2. The device of claim 1 further including, at least one flushing port passing through the housing and located adjacent said first end of the helical cutter.

3. The device of claim 1 further including, anchor means connected to the housing for securely anchoring the device in a passageway of a living organism.

4. The device of claim 1 further including, a guide wire passageway passing through the housing and the helical cutter for receiving a guide wire.

5. An atherectomy device comprising:

a cylindrical housing having a longitudinal axis, the housing having a plurality of slot openings in the housing wall, said slots having a longitudinal direction which is diagonally offset from said longitudinal axis, the housing further having a ferrule having a first end sized to fit within the interior of the housing and establishing a first surface substantially perpendicular to said longitudinal axis;

a helical cutter positioned within the housing, the cutter positioned along and able to rotate around said axis, the cutter having a plurality of blades positioned such that the plurality of blades passes the plurality of slots as the cutter rotates, a first end of the cutter interfacing with said first surface of said ferrule and positioned to squeeze plaque between the cutter and said first surface of said ferrule so as to cut said plaque; and a cutter drive wire passing through a wire aperture in the housing and a passageway in the cutter and aligned along said longitudinal axis, the wire being connected to the cutter for providing rotational movement to said cutter.

6. The device of claim 5 further including, at least one flushing aperture passing through the housing and located adjacent said first end of said plurality of cutting blades so that a piece of matter cut by said blades will be forced through said aperture as the cutter rotates.

7. The device of claim 6 further including, at least one saline aperture passing through the housing and located adjacent said first end of said plurality of cutter blades.

8. The device of claim 7 further including, a catheter connected to and covering a portion of the housing which contains said flushing and saline apertures, said catheter having at least one flushing lumen and at least one saline lumen connected to said flushing and saline apertures, respectively.

9. The device of claim 5 further including, an inflation device connected to the housing for securely positioning the housing in a passageway of a living organism.

10. The device of claim 5 further including, a guide wire passageway passing through the housing and the cutter along said axis for receiving a guide wire.

11. The device of claim 5 wherein, said ferrule has a second end sized to fit within a recessed portion of a catheter.

* * * * *